United States Patent
Falus et al.

(10) Patent No.: US 8,906,856 B2
(45) Date of Patent: Dec. 9, 2014

(54) SINGLE COMPONENT FIBRIN HEMOSTAT

(71) Applicants: George David Falus, New York City, NY (US); Leonid Medved, Ellicott City, MD (US)

(72) Inventors: George David Falus, New York City, NY (US); Leonid Medved, Ellicott City, MD (US)

(73) Assignee: Biomedica Mangement Corporation, Halethorpe, MD (US)

( * ) Notice: Subject to any disclaimer, the term of this patent is extended or adjusted under 35 U.S.C. 154(b) by 0 days.

(21) Appl. No.: 13/731,120

(22) Filed: Dec. 31, 2012

(65) Prior Publication Data
US 2014/0187492 A1    Jul. 3, 2014

(51) Int. Cl.
*A61K 38/36*    (2006.01)
*C07K 14/745*    (2006.01)

(52) U.S. Cl.
CPC ............... *A61K 38/36* (2013.01); *C07K 14/745* (2013.01)
USPC .......................... 514/13.6; 514/13.7; 530/382

(58) Field of Classification Search
None
See application file for complete search history.

(56) References Cited

U.S. PATENT DOCUMENTS 5,739,288 A * 4/1998 Edwardson et al. .......... 530/382

OTHER PUBLICATIONS

Hiemenz, Paul C.; Principles of colloid and surface chemistry, 2nd ed (1986), isbn 0-8247-7476-0.*
Liang, J. Z. and Li, R. K. Y.; "Effedct of filler content and surface treatment on the tensile properties of glass bead filled polypropylene composites." Polym. Int. (2000) 49 p. 170-174.*
Weisel, John. W.; "The mechanical properties of fibrin for basic scientists and clinicians." Biophys. Chem. (2004) 112 p. 267-276.*

* cited by examiner

*Primary Examiner* — James H Alstrum Acevedo
*Assistant Examiner* — Fred Reynolds

(57) ABSTRACT

ClotGel is a single-component hemostatic agent designed for use as an adjunct or primary treatment in moderate intraoperative hemorrhage and in trauma. It can be applied topically to the wound either on the skin in a laparatomy or as non-invasive manner in surgical procedures. Its crosslinking technology generates an adhesive stable fibrin clot using a single component (fibrin II) required for hemostasis. The agent is a mixture of lyophilized polymerized fibrin II and fibrin II monomer which is polymerized and stabilized when in contact with the blood. The attachment properties of the gel, as well as the rapid formation of a fibrin clot, ensures that a strong stable fibrin clot is formed within 1 minute of application.

10 Claims, 5 Drawing Sheets

Figure 4.

Stability Day 0 SDS-PAGE

| Lane number | Sample description |
|---|---|
| 2 | See blue plus 2 standard |
| 4 | C + D, 0 min |
| 5 | C + D, 2 min |
| 6 | C + D, 5 min |
| 7 | C + D, 10 min |
| 8 | C + D, 20 min |
| 9 | C + D, 30 min |

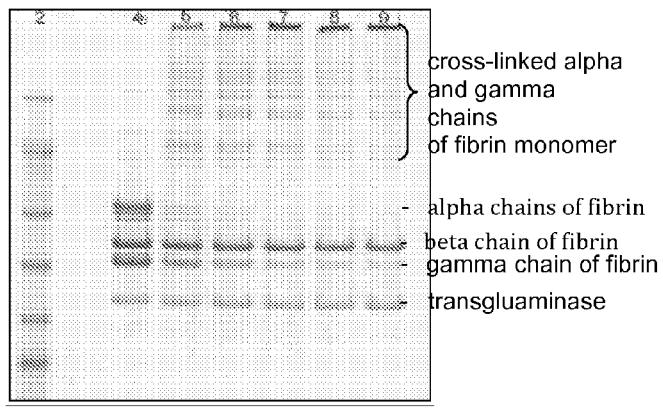

cross-linked alpha and gamma chains of fibrin monomer

- alpha chains of fibrin
- beta chain of fibrin
- gamma chain of fibrin
- transgluaminase

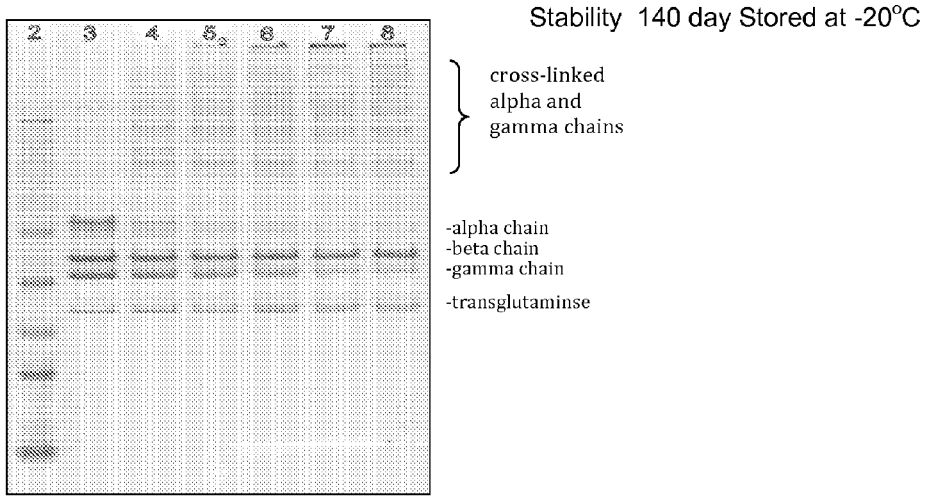

Stability 140 day Stored at -20°C cross-linked alpha and gamma chains

-alpha chain
-beta chain
-gamma chain

-transglutaminse

SINGLE COMPONENT FIBRIN HEMOSTAT

RELATED APPLICATIONS

This application is a Continuation-In-Part of U.S. patent application Ser. No. 12/487,057 (U.S Pat. No. 8,367,802 by G Falus et al.) filed on Jun. 18, 2009 for which a Notice of Allowance was received on Nov. 6, 2012 and with the Issue Fee to be paid before Feb. 6, 2013. All description, drawings and teachings set forth therein are expressly incorporated by reference herein and I claim priority upon the teachings expressly made therein.

FIELD OF THE INVENTION

The present invention is related to a method to produce a sterile biocompatible desAB fibrin polymer (fibrin II) polymer gel-like composition from concentrated desAB fibrin (fibrin II) monomer in acid solution for application as an adhesive sealant component and hemostatic agent. The preparation (invention) trademarked ClotGEL is single component (fibrin) presented in the form of a viscous colloidal solution that may be used to stop bleeding or seal tissue in vivo with and without compression. It s particularly related to a need of incorporating a fibrin sealant in a viscous gel-like product that can resist the flow of blood in a wound without a biodegradable support in order to seal tissue and control vascular, epidermal, bone, or internal hemorrhage.

BACKGROUND OF THE INVENTION

Moderate bleeding for organ resection, some types of trauma, bone fractures, orthopedic procedures, vascular anastomosis, solid organ wounds, and deep dermal wounds often require an adjunct to control the bleeding before or after sutures or stitches are applied.

Current solutions and limitations. Various technologies have been developed for the formulation of hemostats. Some of them contain biological materials such as collagen or fibrinogen and thrombin. As a result of their hemostatic and adhesive properties, fibrin sealants, or thrombin-based products have been extensively used in most surgical specialties for over two decades to reduce blood loss and post-operative bleeding due to their ability to adhere to human tissue as it polymerizes (1, 2, 3). These compounds are used to seal wounds that have been sutured or stapled; they can also be used with pressure over an injured area to control bleeding. Fibrin sealants are biological adhesives that mimic the final step of the coagulation cascade. (4) The main components of the sealant are plasma proteins fibrinogen, and factor XIII on the one hand and thrombin, and calcium chloride on the other. The components are often extracted from human plasma or produced by recombinant techniques. Mixing fibrinogen and thrombin creates a polymer barrier (fibrin) that simulates the last stages of the natural coagulation cascade to form a structured fibrin clot similar to a physiological clot. Products containing thrombin stimulates the coagulation cascade forming a natural fibrin clot.

There are several commercial products available (Floseal, Gelfoam, Evicel, Bioglue) (3, 5). However, these products have limitations such as inflammatory effects, immunological responses, storage conditions, preparation, and need of compression. Most hemostatic agents for intracavitary bleeding are designed to be used in light to moderate bleeding in the operating room and require hard compression. One of the major limitations encountered in the development and/or use of fibrin compositions with brief or no compression is their inability to form a sufficiently strong bond to tissues, to produce a stable clot within minutes of application, and the need to incorporate thrombin and anti-fibrinolitic agents in the formulation. However, there are many situations where the use of strong compression, sutures and/or staples is undesirable, inappropriate or impossible, e.g. in bone, brain, interventional radiology, retroperitoneal surgery. Also the inclusion of thrombin prevents the recover of lost blood.

The present alternative approach: In order to form a physical barrier that resists the flow of blood, the adhesive matrix of fibrin-based hemostat must form in a matter of seconds a strong fibrin interface, bond with tissues in the midst of flowing blood and remain at the lacerated site to form a clot. The ability of ClotGel, produced as a dense colloidal solution similar to a gel, to adhere to human tissue is related to the use of desAB fibrin monomer described in U.S. Pat. No. 8,367,802 by G Falus et al., and its physical properties such as density, composition and method of production of fibrin. Unlike other fibrin sealants that use thrombin to cleave fibrinogen in situ to form a desAB fibrin II (fibrin II) polymer, ClotGel polymerizes desAB fibrin monomer by neutralization in contact with the blood, thus bypassing the cleavage process. The essential aspect of the technology is the ability of crosslinked desAB fibrin (fibrin II) polymer and desAB fibrin (fibrin II) monomer to be mixed with the blood -to form a physical barrier that turns into a functional fibrin clot. (6) In our approach these results are obtained through the in-situ generation of a three-dimensionall polymeric cross-linked fibrin network that is bonded to the tissue as a strong fibrin clot stabilized by Factor XIII present in the blood.

The crosslinked fibrin incorporated into the monomer solution allows to produce a viscous substance that resist the flow of blood, and facilitates transportation and readiness.

Composition. The present technology incorporates crooslinked fibrin polymer produced from neutralized desAB fibrin (fibrin II) monomer, which is then lyophilized, homogenized in neutral buffer, transferred to acid solution, and mixed with fibrin solution kept at pH 3.4. The homogenized polymer-monomer mixture is ready to polymerize at change of pH when in contact with the blood. The desAB fibrin (fibrin II) monomer is produced by the dialysis method (U.S. Pat. No. 8,367,802 by G Falus et al.). The lyophilized crosslinked desAB fibrin (fibrin II) polymer is produced by neutralizing the fibrin monomer with a neutral buffer solution containing calcium chloride, crosslinking with calcium-dependent Factor XIII and calcium-independent transglutaminase enzymes and subsequent Lyophilization.

Mixing blood with the gel-like composition creates a mesh of fibrin fibers that form the fibrin clot at sites of injury (7). Under coagulant conditions, calcium-independent transglutaminase enzyme and activated Factor XIII contribute to this process by stabilizing the fibrin clot through covalent bonds.

Key Attributes. Polymerization/Adhesion. The fibrin gel that seals the wound is formed as a result the absorption of blood, and pH neutralization of the monomer in contact with wound that rapidly turns into polymer of long fibers, trapping the-lyophilized/homogenized fibrin polymer material, which acts as a biocompatible support. The transglutaminase enzyme in the lyophilized component and Factor XIII in the blood leads to further formation of covalent bonds in the clot. The clot is mechanically stable, well integrated into the wound and more resistant to lysis by plasmin compared with uncrosslinked clots [8] or other fibrin sealants. The inclusion of calcium-independent transglutaminase enzyme facilitates the transglutaminase-mediated oligomerization of the αC-domains of fibrin promoting integrin clustering and thereby increasing cell adhesion and spreading, which stimulates fibrin to bind αvβ3-, αv-β5-and α5-β1-integrins on endothelial cells (9). The oligomerization also promotes integrin-dependent cell signaling via focal adhesion kinase (FAK) and extracellular signal-regulated kinase (ERK), which results in an increased cell adhesion and cell migration [10].

The adhesion characteristics to vital human tissue and the kinetics of polymerization of the proposed agent have been tested in vitro and in vivo. The data obtained provide ample evidence of the ability of ClotGel to stop bleeding and achieve hemostasis with and without compression in four surgical protocols including vascular anastomosis, knee replacement, liver and kidney laceration/resection and spleen lacerations in the swine models. The polymerization process begins within 6 seconds of application.

Fibrin Monomer Polymerization:

U.S. Pat. No. 8,367,802 by Falus et al. describes a method of preparing a fibrin monomer. The ClotGel sealant composition uses a lyophilized crosslinked fibrin polymer obtained by neutralizing of fibrin monomer, which is mixed with fibrin monomer. The composition of parts and method of production of the fibrin monomer described in this patent application as well as the process of neutralization and crosslinking of the polymer are critical to the performance of the proposed technology, which depends on the characteristics of fibrin itself (thickness of the fibers, the number of branch points, the porosity, and the permeability. The clot produced by ClotGel creates opaque matrices of thick fibers, and, therefore, formation proceeds at a faster rate than in transparent matrices. The concentration of thrombin to produce a fibrin monomer also has an important impact on the polymerization process.

ClotGel Presentations:

The fibrin suspension can be presented in several dosages, from 5 cc to 20 cc in order to adapt to the type of application (FIG. 1).

SUMMARY OF THE INVENTION

The present invention lies within the domain of biological tissue sealants and hemostats, which are biodegradable and nontoxic, intended for therapeutic use, for example, as an adjunct to hemostasis in laparotomy or laparoscopic surgery, in orthopedic surgery, trauma (spleen laceration), and large-bed wounds.

In one aspect, the present invention relates to biocompatible adhesive fibrin polymer, which is bio-reabsorbable and nontoxic, for surgical or therapeutic use. It also relates to a single-part application containing a single bioactive substance (fibrin) which can be released in a given site to produce a stable fibrin clot.

In another aspect, the invention relates to a process for producing a viscous adhesive that can resist the flow of blood.

Extensive in vivo studies show that ClotGel is an excellent general hemostatic agent candidate for use as adjunct and primary treatment in moderate bleeding. The agent is durable, easy to store, poses minimal risk, requires little training to use, and is highly effective against bleeding.

BRIEF DESCRIPTION OF THE DRAWINGS

FIG. 4. SDS-PAGE of fibrin monomer polymerized

DETAILED DESCRIPTION

Figure 1:
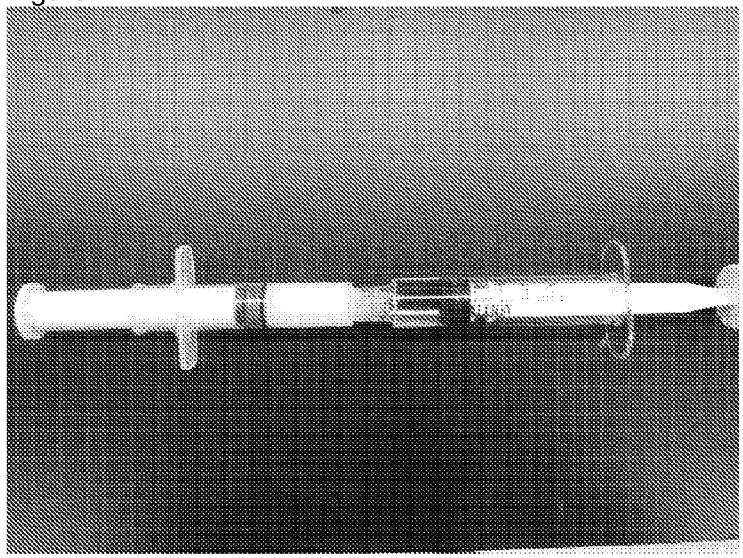
FIG. 1. Clotgel presentation in mixing syringes.

ClotGel is a hemostatic agent and tissue sealant made of a single chemical entity, for use as an adjunct to hemostasis or primary treatment in surgical procedures and in treatment of traumatic wounds.

ClotGel is a novel fibrin sealant depleted of thrombin and without any other collagen or polymer support, designed to create hemostasis through the formation of a stable fibrin clot with or without compression when in contact with blood.

ClotGel consists of a lyophilized crosslinked fibrin polymer homogenized and suspended in fibrin monomer. The lyophilized fibrin polymer is produced by neutralization of fibrin monomer in acetic acid solution (pH 3.4) with HEPES buffer (pH 8.3); crosslinked calcium ions.

The suspension is applied over lacerated bleeding tissue, forming a sticky, gummy gel barrier and subsequently a fibrin clot as blood is absorbed by the composition. The agent seals the wound with a semi-solid cap to form a blood clot within 1 minute, and binds together the lacerated tissue.

Composition, Manufacturing and Application of ClotGel

ClotGel consists of two components: 1) A lyophilized desAB fibrin II (fibrin II) polymer, and 2) a desAB fibrin (fibrin II) monomer in acetic acid solution at a concentration of 24 mg/ml. Each component is stored in a separate syringe, which are mixed before usage to produce a single viscous gel-like product.

To produce the fibrin polymer, 12 mg/mL to 24 mg/ml of sterile desAB fibrin (fibrin II) monomer in acetic acid solution, pH 3.5, made by the dialysis manufacturing process (U.S. Pat. No. 12/487, 057) is mixed with neutralization buffer solution composed of 100 mM HEPES, pH 7.7, 150mM NaCL, 5 mM CaCl, 0.12 g/mL Activa (calcium-independent transglutaminase enzyme). The two solutions are mixed in a 1:1 ratio inside a sterile mold. This mold is sealed inside a sterile tyvek bag and incubated at 37° C. for four hours. The polymer still in the mold in the tyvek bag is then frozen at −80until solid.

The fibrin polymer is lyophilized in the same tyvek bag sealed to reduce contamination at a condenser temperature of −40° C. to −50° C., shelf temperature of 21° C. , for 18-72 hours at a pressure of 200-400 millitor.

The lyophilized fibrin polymer is pulverized into a powder using a sterile mortar and washed repeatedly with pH 3.4 acetic acid solution, until final pH of the paste is 3.4 to 3.5. The pellet paste is centrifuged to remove up to 80% of the acid solution.

The paste is filed into a female luer lock syringe of the type Quosina Part C3603 or similar.

The fibrin monomer is produced according to the method described in U.S. Pat. No. 8,367,802and sterilized by filtration through a 0.22 micron Millipore filter. The fibrin monomer is then filed into a male luer lock syringe type Quosina Part C1009 or similar.

Before use the parts are mixed (homogenized) into a single syringe at a proportion of 2:3 polymer to monomer.

EXAMPLES

The adhesion characteristics to vital human tissue, the kinetics of polymerization of the gel, biocompatibility, stability and clotting efficacy tests show that ClotGel sealant forms a strong fibrin clot within 1 minute of application over a bleeding wound. The agent is biocompatible, has a 180 days stability, and adheres to lacerated tissue binding the opposing tissues together with a strength that is significantly higher than that observed for other tested fibrin sealants. The following tests were conducted in vitro and in vivo (rat, rabbit and swine models).

1. Molecular Chemistry of Fibrin Polymerization

We conducted molecular chemistry assays to: 1) Establish the clotting time; 2) Determine the clotability of the fibrin monomer within the ClotGel Mix; and 3) compared the effectiveness of fibrin monomer polymerization (pH Neutralization) and stabilization (cross-linking) by activated Factor XIII versus stabilization by Factor XIII and calcium-independent tranglutaminase enzyme (ACTIVA); and 4) Determine that the homogenized mix was able to polymerize in the form of long fibrin fibers.

1.1 Studies to Establish the Clotting Time

Figure 2:
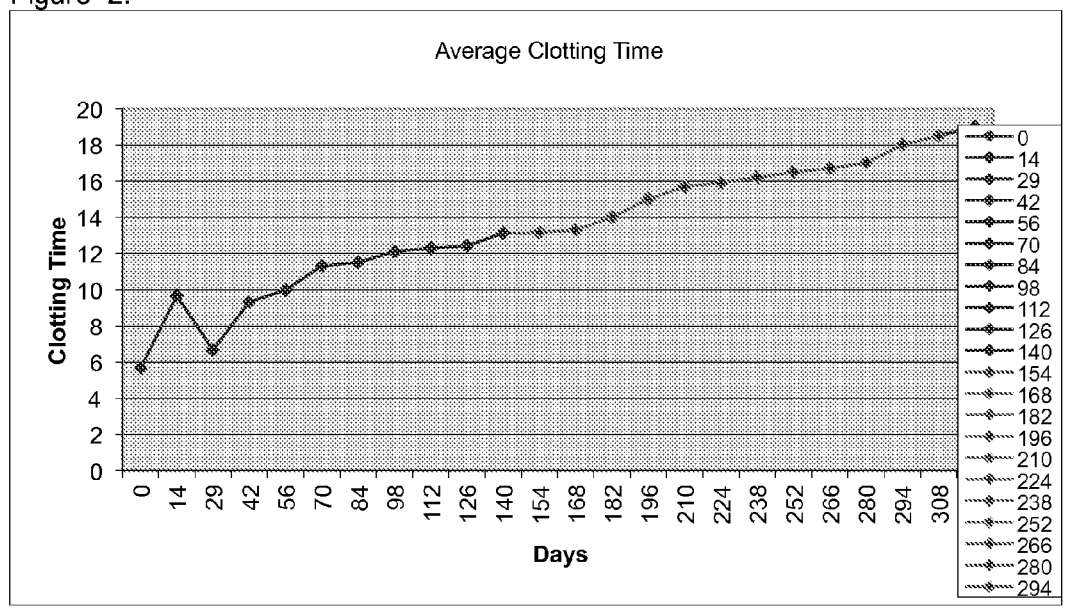
FIG. 2. Average clotting time of fibrin monomer stored at 31 20° C.

In order to determine the time fibrin requires to clot, 250 ul of Part C are mixed with 750 ul of neutralization buffer. The clotting time is recorder with a timer. Three experiments are performed for each condition and averaged out. FIG. 2 shows that clotting time varies between 9 and 20 seconds overtime when stored at −20° C. The blue line indicates actual testing (up to 140 days) and red a projection up to 320 days.

1.2. Studies to Determine the Clottability of the Fibrin Monomer within the ClotGel Mix The fibrin polymer formed during clotting time study is kept for 20 min for maturation, then squeezed to get the possible liquid out, and tested for Clottability. Three experiments are performed for each condition and averaged out. The optical density of the liquid is measured in a spectrophotometer and the % Clottability is calculated as follows:

Concentration of part C before polymerization—Concentration of part C in the squeezed liquid *100

Concentration of part C before polymerization

Figure 3:
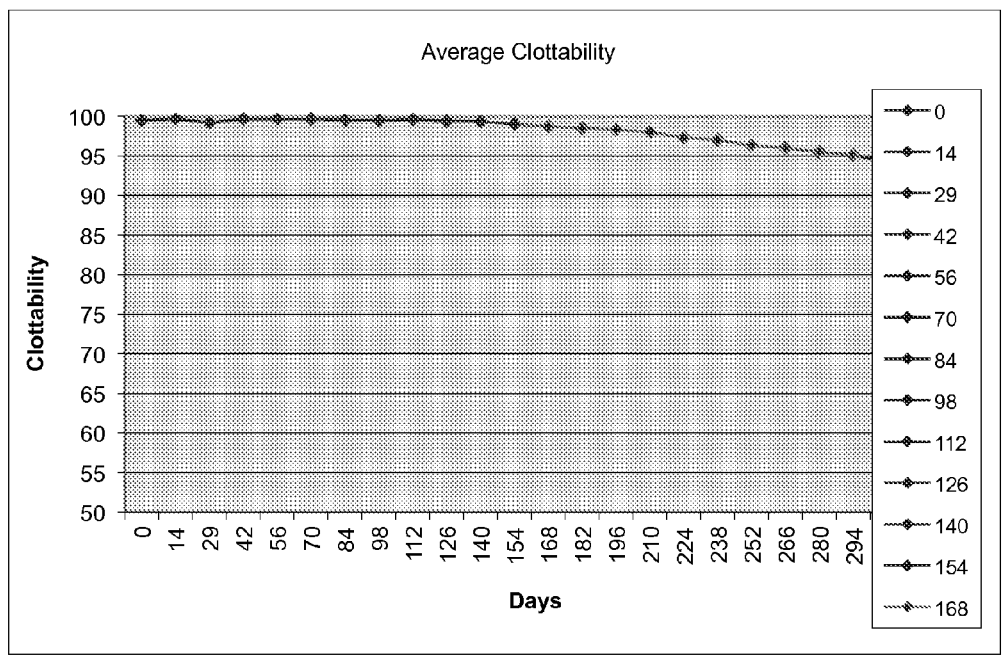
FIG. 3. Clottability of fibrin monomer refrigerated, and at room temperature.

FIG. 3 shows the average clottability when stored at −20° C. over time 1.3. Clotgel Polymerization The polymerization ability of Clotfoam components is established by SDS-PAGE. In order to conduct the study, 22 ul of Part C, 22 ul of PartD and 56 ul of neutralilzation buffer are mixed and incubated for 0, 2, 5, 10, 20 & 30 min. At each time point, the polymerization reaction is stopped with 100 u1 of 8 M urea, and the sample is diluted with 800 u1 of 4 M urea.

The gel is run for 35 minutes at 200V, stained for 1 hour and washed until the sample becomes clearly visible. Stability at day 140 when stored at −20° C. is shown in FIG. 4.

1.4. Studies to Determine the Catalyzing Effect of ACTIVA on Fibrin Stabilization within ClotGel.

Figure 5:
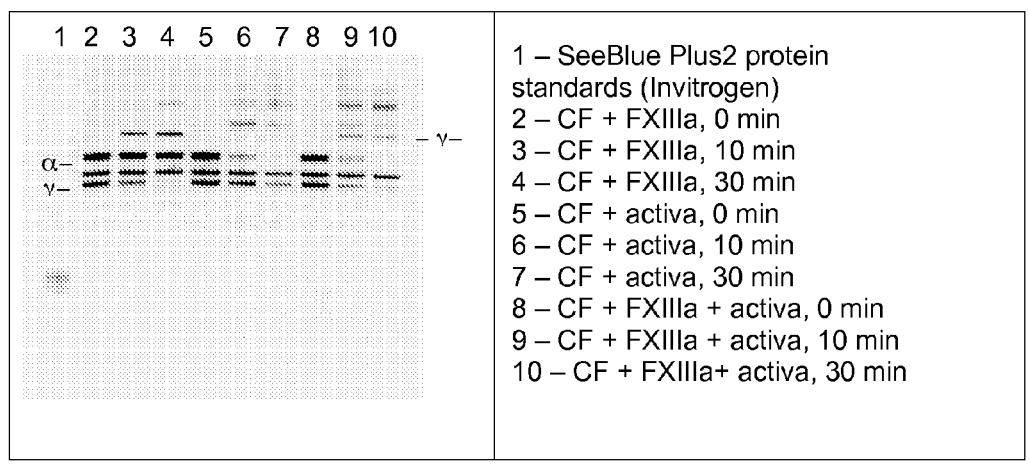
FIG. 5. Polymerization, cross-linking and stabilization of fibrin in the presence of Activa, Factor XIII and Activa+factor XIII FIG. 6. Confocal Microscopy of Polymerized ClotGel FIG. 7. Biocompatibility experiments performed in human fibroblast (HF) cultures exposed to ClotGel preparations. (a) HF—Untreated, Day 5; (b) HF+Clotgel, Day 5.

We conducted studies to compare the effectiveness of fibrin monomer polymerization (pH Neutralization) and stabilization (cross-linking) by activated Factor XIII versus stabilization by Factor XIII and Ca Independent tranglutaminase enzyme (ACTIVA). Results are described in FIG. 5.

It is well established that FXIII in the presence of $Ca^{2+}$ catalyzes fibrin monomer conversion into insoluble fibrin clot. However, whether the presence calcium independent transglutaminase enzyme in the reaction mixture catalyzes crosslinking of free fibrin momomer was not established. Nor has it been previously established that there is a synergistic effect of calcium independent transglutaminase enzyme and activated Factor XIII. In order to follow these reactions, fibrin monomer was subjected to calcium independent transglutaminase enzyme treatment, first as a concentration dependent reaction and later as a time dependant reaction.

Concentration-dependent and Time-dependent monitored reaction (1, 5,10 min, respectively), A volume of acidic solution of 2mg/ml fibrin was quickly mixed with Activa in 60 mM Tris buffer (pH 8.4, w/ 2 mM $CaCl_2$) in variable concentration (1.0-20.0 U/ml) to achieve neutralization. The samples in each lane were incubated for 10 min at 37° C. The samples was electrophoresed and transferred to nitrocellulose membrane. The Fibrin was visualized with anti-fibrinogen antibody (1:50). As expected, quick neutralization of fibrin with buffer generated a number of cross-linked fibrin molecules (lanes 2, 3, 5) with increased concentration of calcium independent transglutaminase enzyme incorporated in it when compared with lane 1 containing control sample of fibrin. Furthermore, fragmented derivative products (FDP) of lower molecular weight bands also participate in crosslinking, in addition to high molecular weight dimers and tretramers.

Assays compared a) fibrin and fibrinogen crosslinking by calcium independent transglutaminase enzyme at 1, 5 and 10 Minutes (FIG. 5) and fibrin crosslinking by calcium independent transglutaminase enzyme at concentrations of 20 u/ml, 19 U/ml, and 1 U/ml.

The figure shows the formation of strong gamma dimers during fibrin cross-linking with calcium independent transglutaminase enzyme and factor XIII at 1 minute. At this time gamma dimmers are not yet present in the fibrinogen sample.

Figure 6:
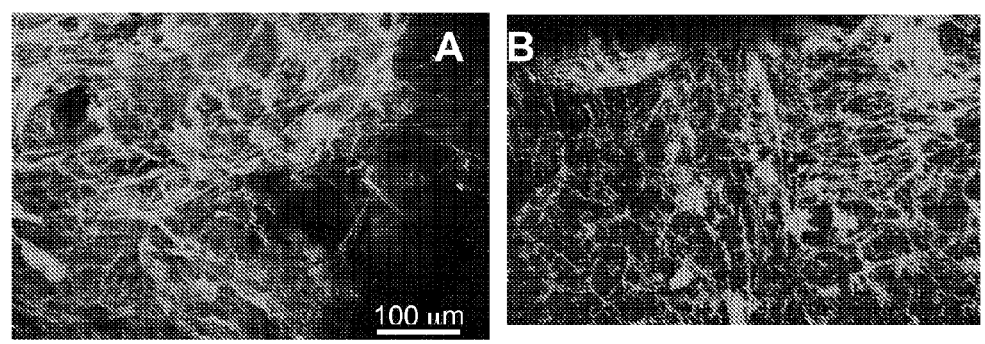

1.5. Studies to Determine that the Homogenized Mix Polymerizes in the Form Of Long Fibrin Fibers as shown in Confocal Microscopy in FIG. 6.

2. Biocompatibility

Figure 7:
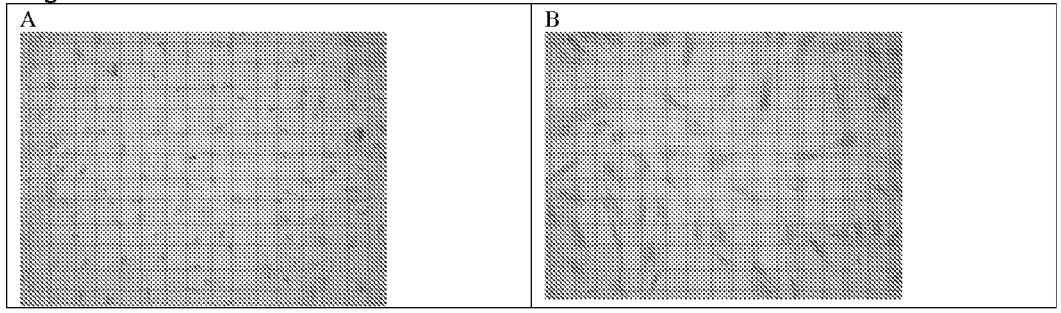
Figure 8:
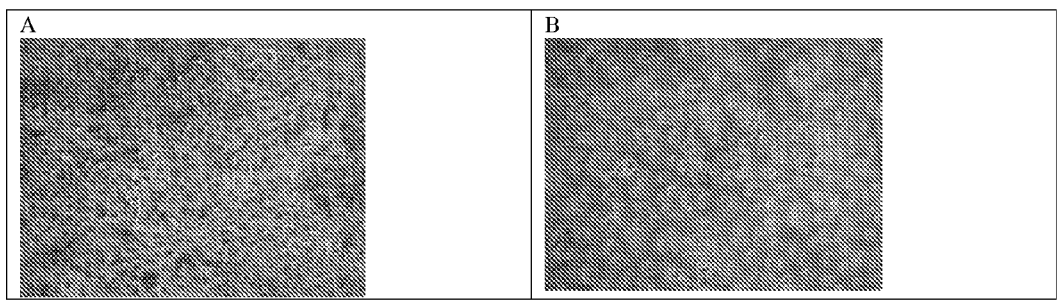
FIG. 8. Biocompatibility experiments performed in human epithelial cell cultures (A549) exposed to ClotGel preparations. (a) A549 cells—Untreated, Day 5; (b) A549cells+ClotGel, Day 5.
Figure 9:
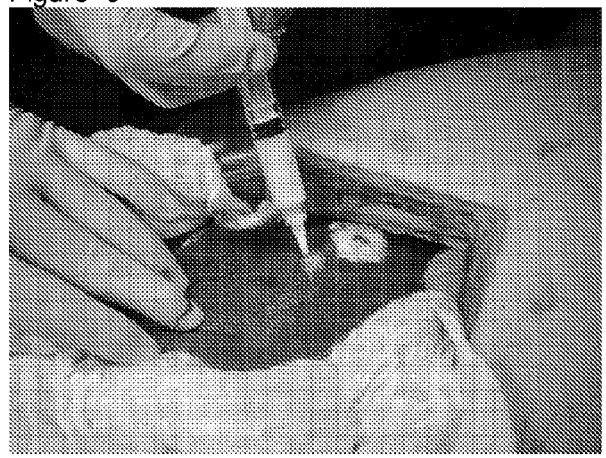
FIG. 9. ClotGel applied over a lacerated surface

ClotGel was tested for biocompatibility with human fibroblasts (HF) as shown in FIG. 7 and human epithelial cells (A549 cell line, ATCC) as shown in FIG. 8. Normal human fibroblasts (HFs) were obtained from a commercial source and cultures established in 60 mm tissue culture plates in Dulbecco's modified Eagle's medium supplemented with 10% fetal bovine serum and maintained at 37° C. in a humidified 5% $CO_2$ atmosphere ($CO_2$ incubator). Human epithelial cell line A549 was maintained in Minimal Essential Medium supplemented with 10% fetal bovine serum and 2 mM glutamine. When fibroblast and epithelial cell cultures reached subconfluence, control and sodium benzoate ClotGel preparations were placed into individual dishes. The cultures were returned to the $CO_2$ incubator and examined daily for a total of five days. ClotGel material and medium was removed from all cultures, and adherent cells were stained with crystal violet (0.1% in 2% ethanol).

The main observation was a total absence of damage or toxicity to the cells, and absence of any bacterial or fungal contamination. In human fibroblast cultures exposed to ClotGel preparations, the cells appeared slightly larger or more spread out than in control untreated cultures. Conclusion: ClotGel is biocompatible, and do not affect, but rather stimulate, the growth and differentiation of cells; which is an important attribute in wound healing agents.

3. Efficacy in Animal Models

We conducted studies on intracavitary intraoperative bleeding in the swine (pig) model.

Study objectives: Compare ClotGel versus standard surgical practice and Floseal in stopping moderate to severe bleeding in spleen laceration and liver resection 3.1. Evaluation of ClotGel for the Control of Spleen Laceration Bleeding as Primary Treatment without Packing or Sutures.

The purpose of this study is to determine if CloGel can stop profuse bleeding within 5 minutes of application in cases traumatic spleen laceration. Methods: Six female Yorkshire crossbred swine, age 2.5 months, weighing 37±2 kg, were used. The protocol was approved by the Institutional Animal Care and Use Committee. Animals were subject to a 1 inch incision in lateral middle portion of the spleen (created sharply by an 11 blade scalpel). After the damage was induced, a 10 mL of ClotGel composition was compressed against the laceration for 2 minutes. Hemostasis was achieved in all animals within 5 minutes of application. Results: All animals (n=6) Achieved hemostasis within 5 minutes of application* with a median of 3.2±1.4 min. None of animals treated with Floseal (Baxter) achieved complete hemostasis.

* The five minute time to hemostasis is defined by the Blood Products Committee of the Food and Drug Administration as the maximum time to demonstrate efficacy in achieving hemostasis.

3.2. Evaluation of ClotGel for the Control of Intraoperative Bleeding as Adjunct Treatment in Liver Injury.

Two groups of Six female Yorkshire crossbred swine, age 2.5 months, weighing 37±2 kg, underwent a 2.5 Inch liver biopsy via open laparotomy, A spot in the middle of the liver was selected to produce the liver injury with a scalpel. The position was calculated by approximation to the suprahepatic vessels and some branches of the portal vein. The spot was marked with a marker. In Group 1 the resection treated with a 5 mL ClotGel and compresed for 10 seconds over the wound. In group 2 (n=6) the same resection was treated with Floseal and compressed for 2 minutes against the wound. Results: In both groups hemostasis was achieved in all animals within 5 minutes of application.

4. Pharmacokinetic Profile of the Agent through Biodegradation studies.

Elimination through biodegration by proteolytic enzymes was determined in vivo .

Method: To examine the fate of ClotFoam in vivo, a batch of ClotGel was prepared using fluorescein-tagged human fibrinogen as tracer. This preparation of ClotGel was applied to the six animals of Group 1 in the liver grade IV wound procedure (4.3), which were euthnanized at 2 weeks (n=3) and 4 weeks (n=3) following application. Once animals are sacrificed, organs were collected, fixed in 10% formalin and embedded in paraffin blocks. Histologic sections were examined at 100 X and 400 X in fluorescence microscope. The elimination of ClotBlock was determined by either the total absence of fluorescent traces in the samples, or by the level of fluorescense observed at 2 weeks and 4 weeks.

Results: ClotGel was eliminated in all organs within 4 weeks of application.

5. Sterilization

Sterile preparations of ClotGel were studied.

The acidic Fibrin Monomer was sterile filtered in a biological safety cabinet using a Nalg-Nunc 500 mL device (Cat # 450-0045, nitrocellulose membrane, 0.45 m filter). The Lyophilized polymer component was sterilized also by filtration prior to lyophilization.

Growth Study: The general experimental protocol included preparation of sample solutions which were then plated on Potato dextrose agar (PDA, Sigma-Aldrich, Cat#P2182) and Tryptic soy agar (TSA, Sigma-Aldrich, Cat# T4536) gels in Petri dishes for growth. The PDA and TSA gels were incubated and observed at the indicated periods of time for colony growth (mold and/or bacteria).

The sample was incubated for 30 min at 37° C. and evaluated for colony growth using the naked eye at the time periods indicated in the Results and Discussion section. The samples were run in duplicate or triplicate with multiple samples indicated with a 1, 2 and 3 designation in data tables. The scale used for evaluation is as follows:

TABLE 2

Colony Count Key

| Symbol | Count |
|---|---|
| − | No visible growth |
| + | 1-199 visible colonies |
| ++ | 200-399 visible colonies |
| +++ | >400 visible colonies |

Table 3 shows the results of studies of microorganism growth analysis on PDA and TSA of the sterile components of FIBRIN_ClotFoam.

TABLE 3

Sterilization Studies by Bacterial Growth on PDA/TSA at 37° C.

| | | Time Elapsed (days) | | | | | | | | | | | | | | |
|---|---|---|---|---|---|---|---|---|---|---|---|---|---|---|---|---|
| | | Potato Dextrose Agar (PDA) | | | | | | | Tryptic Soy Agar (TSA) | | | | | | | |
| Sample | | 1 | 2 | 3 | 4 | 5 | 6 | 7 | 11 | 1 | 2 | 3 | 4 | 5 | 6 | 7 | 11 |
| C** | 1 | | | | − | | | − | − | | | | − | | | − | − |
| (Fibrin/ | 2 | | | | − | | | − | − | | | | − | | | − | − |
| AcOH, pH | 3 | | | | \! | | | − | − | | | | − | | | − | − |
| 3.5) | | | | | | | | | | | | | | | | | |

**stored at 4° C. for seven days

The growth data indicate that sterile components yielded no significant growth even after 11 days. Furthermore, the following techniques could be used for sterilization.

What is claimed is:

1. A composition for the control of bleeding with or without compression comprising the following two components homogenized into a single colloidal solution at the time of use:

a) a crosslinked lyophilized/homogenized desAB fibrin (fibrin II) polymer suspended in acetic acid solution at a concentration ranging from 6 mg/mL to 24 mg/mL, b) a des AB fibrin (fibrin II) monomer in acetic acid solution or sodium acetate at a concentration ranging from 6 mg/mL to 24 mg/mL, wherein the acetic acid solution or sodium acetate buffer has a pH of 3.4-4.0.

2. The composition as claimed in claim 1 wherein the lyophilized fibrin polymer is washed with acetic acid solution in order to adjust final pH value to 3.4-3.5.

3. The composition as claimed in claim 1 wherein prior to lyophilization, the fibrin polymer is crosslinked in the presence-of calcium-independent transglutaminase enzyme.

4. The composition as claimed in claim 1 wherein both the fibrin monomer and the fibrin polymer are depleted of thrombin by a dialysis process.

5. The composition as claimed in claim 1 wherein the components can be rendered sterile, are non-toxic, do not affect growth of human fibroblasts (HF) or human epithelial cells and therefore is characterized as being biocompatible and suitable for human use.

6. The composition as claimed in claim 1, wherein when applied over the wound and becoming in contact with blood, it results in the formation of a covalently bonded fibrin clot made of fibrin fibers that seals the wound.

7. A method to prepare a composition for the control of bleeding, with or without compression, the method comprising the steps of:
   a) preparing a des AB fibrin (fibrin II) monomer in acetic acid solution at a concentration ranging from 6 mg/mL to 24 mg/mL, where the acetic acid solution has a pH of 3.4-3.5.
   b) mixing a crosslinked lyophilized/homogenized desAB fibrin (fibrin II) polymer in acetic acid solution at a concentration ranging from 6 mg/mL to 24 mg/mL, and
   c) homogenizing the composition, whereby the composition is characterized as a colloid.

8. The method as claimed in claim 7, wherein the lyophilized/homogenized fibrin polymer is prepared by the step of washing the lyophilized polymer with acetic acid solution at a pH of 3.4-3.5.

9. The composition as claimed in claim 6 wherein rapid polymerization and crosslinking of the fibrin polymer occurring within two minutes of application of the composition to the wounded tissue achieves hemostasis within 5 minutes of application depending on the severity of the wound.

10. The composition as claimed in claim 1 wherein biodegradation is achieved within 4 weeks of application.

* * * * *